United States Patent
Giordano et al.

(10) Patent No.: US 10,857,388 B2
(45) Date of Patent: Dec. 8, 2020

(54) RADIATION THERAPY WITH IMMUNE RESPONSE MONITORING

(71) Applicants: Carl Zeiss Meditec AG, Jena (DE); Klinikum Mannheim GmbH, Mannheim (DE)

(72) Inventors: Frank Giordano, Dudenhofen (DE); Matthias Benker, Heidenheim (DE); Matthias Ahlgrimm, Barsbüttel (DE)

(*) Notice: Subject to any disclaimer, the term of this patent is extended or adjusted under 35 U.S.C. 154(b) by 381 days.

(21) Appl. No.: 15/836,702

(22) Filed: Dec. 8, 2017

(65) Prior Publication Data
US 2018/0169438 A1   Jun. 21, 2018

Related U.S. Application Data

(60) Provisional application No. 62/435,405, filed on Dec. 16, 2016.

(51) Int. Cl.
| | | |
|---|---|---|
| *A61N 5/10* | (2006.01) | |
| *C12Q 1/6886* | (2018.01) | |
| *G01N 33/574* | (2006.01) | |

(52) U.S. Cl.
CPC .......... *A61N 5/1048* (2013.01); *A61N 5/1038* (2013.01); *C12Q 1/6886* (2013.01); *G01N 33/574* (2013.01); *G01N 33/57407* (2013.01); *A61N 2005/1091* (2013.01)

(58) Field of Classification Search
CPC .......... A61N 2005/1091; A61N 5/1038; A61N 5/1048; C12Q 1/6886; G01N 33/574; G01N 33/57407
See application file for complete search history.

(56) References Cited

U.S. PATENT DOCUMENTS

| | | | | |
|---|---|---|---|---|
| 2003/0204069 A1* | 10/2003 | Morin | .................... | C07K 16/40 536/23.2 |
| 2012/0004492 A1* | 1/2012 | Weibrecht | .............. | A61N 5/103 600/1 |
| 2015/0196628 A1* | 7/2015 | Mason | .................... | A61K 35/74 600/1 |

FOREIGN PATENT DOCUMENTS

WO   WO2014033263 A1   3/2014

OTHER PUBLICATIONS

Gebhardt, et al., "Myeloid cells and related chronic inflammatory factors as novel predictive markers in melanoma treatment with ipilimumab," Clin. Cancer Res. 21(24):5453-5459) (2015).
Keilholz, et al., "Immune monitoring of T-cell responses in cancer vaccine development," Clin. Cancer Res. 12(7 Suppl): 2346s-2352s (2006).
Sharabi, et al., "Stereotactic radiation therapy combined with immunotherapy: augmenting radiation's role in local and systemic treatment," Oncology (Williston Park), 29(5):331-40, May 2015.

(Continued)

*Primary Examiner* — Christine H Matthews
(74) *Attorney, Agent, or Firm* — FisherBroyles, LLP; James W. Hill

(57) ABSTRACT

A method of treating cancer includes administering a first dose of radiation to a subject; determining a level of a biomarker obtained from the subject, the level indicating an immune response of the subject to the first dose; and not administering a second dose of radiation to the subject unless and until the level of the biomarker is beyond a threshold value.

16 Claims, 1 Drawing Sheet

(56) References Cited

OTHER PUBLICATIONS

Van Allen, et al., "Genomic correlates of response to CTLA-4 blockade in metastatic melanoma," Science 350(6257):207-211 (2015).
Zhang, et al., "Antigenic profiling of glioma cells to generate allogeneic vaccines or dendritic cell-based therapeutics," Clin. Cancer Res. 13(201):566-575 (2007).

* cited by examiner

RADIATION THERAPY WITH IMMUNE RESPONSE MONITORING

CROSS-REFERENCE TO RELATED APPLICATION

This application claims the benefit of U.S. Provisional Application No. 62/435,405, filed Dec. 16, 2016, which is incorporated herein by reference in its entirety.

TECHNICAL FIELD

The subject technology generally relates to treating cancer using radiation therapy.

BACKGROUND

Cancerous tumors can grow and metastasize, leading to medical complications including death. Therapies that slow, delay, or reverse tumor development are valuable for their benefits to patients.

SUMMARY

Treating cancer patients with irradiative therapy confers an immediate tumoricidal benefit to the irradiated target. Treating a patient with a well-directed dose of radiation provides the added benefit of triggering the patient's anti-tumor immune response. This response may be hampered by subsequent radiation therapy or chemotherapy that is administered before the immune system is able to develop an adequate response.

The instant technology involves a method of treating a patient with a single dose of radiation followed by monitoring the patient's immune response to determine later treatment of the patient. The administration of the treatment is, in some cases, performed intraoperatively. The treatment may be paired with therapies that enhance the immune system's response or depress regulation of the immune system. Monitoring the immune response of the patient may allow for the delay or avoidance of additional radiation therapy or chemotherapy, increasing the subsequent immune response.

The subject technology includes a method of treating cancer, comprising administering a first dose of radiation to a subject having cancer; determining a level of a biomarker obtained from the subject after the administering, wherein the level indicates an immune response of the subject to the first dose; not administering a second dose of radiation to the subject when the level is not beyond a threshold value; and administering the second dose to the subject when the level is beyond the threshold value. "Beyond" a threshold value can mean higher or lower than the value, depending on the context.

In some embodiments, the first and second doses are part of a predetermined fractionated or hypofractionated dose for the subject. In some embodiments, the level indicates an amount or an activity (of a protein or its sub-fractions) of at least one of interleukin-13 receptor α2, IL13α2, Mage-1, high mobility group box 1 protein, Aim-2, tyrosinase, tyrosinase-related protein 1, Trp-1, Trp-75, Trp-2, Gage, human melanoma-associated antigen p97/GP100, melano-tranferrin, Her2/neu, B-cyclin, EphA2/Eck, telomerase reverse transcriptase, hTert, Sart-1, survivin, GnT-V, or Mart-1.

In some embodiments, the second dose is administered to a different location in the subject than was the first dose. In some embodiments, the biomarker is obtained from at least one of serum, cerebrospinal fluid, peritoneal fluid, or urine. The biomarker may be a protein, protein fragment, peptide, peptide fragment, DNA, DNA fragment, RNA, RNA fragment, other nucleic acid or nucleic acid fragment, or any other substance, structure, or process that can be measured in the body or its products. In some embodiments, the cancer comprises a glioma or a metastatic brain tumor. Other cancers may also be treated with the method.

Additional objects and advantages of the present invention will be clear from the description that follows.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

BRIEF DESCRIPTION OF THE DRAWINGS

A more complete appreciation of the subject technology and many of its advantages will be understood by reference to the following detailed description when considered in connection with the following drawings, which are presented for the purpose of illustration only and are not intended to be limiting, and in which:

FIG. 1 shows the distant response in a patient after intraoperative radiation therapy (IORT) plus standard of care therapy.

DETAILED DESCRIPTION

The following explanations of terms and examples are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

Described herein are methods to apply high-dose ionizing radiation to a target in a patient thereby treating the patient followed by monitoring the patient's immune response. By applying a single dose radiation therapy, the instant method irradiates a target with a high dose of radiation destroying cancerous cells at the target and conferring an anti-metastatic benefit to tumorous regions both inside and outside of the target. By employing these methods, a higher single dose may be provided, increasing the abscopal effect and decreasing undesirable targeting of healthy tissue. Monitoring the patient's immune response allows for an immune-response-specific treatment.

Targets refer to any tissue or location that it may be desirable to irradiate in order to achieve beneficial effects for the treatment of the patient. Targets include but are not limited to internal tumors, external tumors, one of multiple cancerous lesions, a portion of a tumor or lesion that is less than the whole tumor or the whole lesion, a tumor bed, or tissue proximal to a tumor, lesion, or tumor bed. It is envisioned that the instant methods may be especially helpful in treating multiple lesions in the brain, such as glioblastoma or metastases from breast, melanoma, lung, or colon cancer.

Intraoperative application of irradiation therapy allows for accurate and precise control over the irradiation therapy that exceeds control available to external irradiation. The ability to precisely and accurately direct the irradiation during IORT enables an operator to direct a dose of radiation at a small, localized target. This increases the antineoplastic effect of therapy by concentrating irradiation to a target and reduces undesirable irradiation of healthy or non-cancerous cells or tissues outside of the intended target. An aspect of the instant methods is the ability to avoid undesirable irradiation to tissue responsible for maintaining a patient's white blood cell counts, such as in bone marrow and blood.

The instant method's accuracy and precision allow for radiation treatment comprising a higher dose than that feasible with external irradiation. Such a high tumoricidal dose would increase the direct antineoplastic effect, eliminating cancerous cells efficiently within the target. Additionally, the high dose would trigger the systemic or local antineoplastic immune effect. This effect would provide an immune system response to distal tumors, distal lesions, tissue connected to but not within the irradiation target, and other cancerous tissues and cells not within the therapeutic area of influence respond to the therapy, allowing for treatment at a distance.

The "high" dose of the treatment may be any dose high enough to trigger a systemic or local neoplastic immune effect of the patient, either alone or in concert with immune modulatory therapies. Dose levels may be 3 Gy or greater. In one embodiment, the dose may be between or about 3 Gy and 5 Gy. In another embodiment, the irradiation dose may be between about 5 Gy and 10 Gy. In another embodiment the dose may be higher than 10 Gy, up to 12 Gy, or up to 15 Gy. In another embodiment the radiation dose may be as high as 20 Gy. In a another embodiment the radiation dose may be between about 20 Gy and about 40 Gy. The dose may surpass 40 Gy in other embodiments.

The "dose levels" described above refer to a dose applied at a nearest surface of the tissue being irradiated. It is understood in the field that different radiation amounts provided at different distances can result in identical dose levels received in a tissue. For example, a dose of 20 Gy administered at the surface of a tumor bed and a dose of 6 Gy administered at a 1 cm distance within the tissue may share the same target dose profile and produce the same dose, i.e., dose level. A dose level applied before, during, or after an invasive medical procedure including a surgery or operation refers to a dose applied at the tumor bed, surgical margin, or nearest tissue to which the irradiation is applied.

In preferred embodiments, the irradiation will be provided by low-energy photons. In an embodiment, the irradiation is performed with photons with energies less than 10 kV. In another embodiment, the irradiation is performed with photons with energies between 10 kV and 50 kV. In another embodiment, the irradiation is performed with photons with energies greater than 50 kV and less than 120 kV.

In a preferred embodiment of the method, the irradiation is administered in a single dose. In another embodiment, the irradiation dose may be administered by conventional fractionation or hypofractionation. In hypofractionation, the total dose is administered in a shorter course of larger doses than in conventional fractionation.

The irradiation dose may be applied at any time during a medical procedure. Such procedures include any surgery or operation. The dose may be applied before or during tumor resection or biopsy. In an embodiment, the irradiation therapy is applied after the tumor resection or biopsy. In another embodiment, the therapy is applied during a surgery or operation or other medical procedures that do not result in a tumor resection or biopsy.

It is envisioned that irradiation treatment may not be limited to intraoperative irradiation. In an embodiment high dose irradiation may be performed on targets at or near the surface of a patient's skin, such as melanoma, or other external organs without the need for an invasive medical procedure. In such embodiments it is envisioned that the patient will benefit from both the tumoricidal and abscopal effects of the treatment. These patients will also benefit from the limitation, delay, postponement, or avoidance of post-treatment external radiation therapy or chemotherapy, as will patients who receive intraoperative irradiation therapy.

Application of Irradiation

Any suitable instrument known in the art may be used to irradiate a target. In an embodiment, the instrument generates directed, highly ionizing radiation. In a preferred embodiment, the instrument generates x-rays. In some embodiments the instrument uses tungsten, molybdenum, rhodium, or any other appropriate material as the anode material to generate x-rays or other ionizing radiation. Suitable instruments are known to persons of skill in the art.

In addition to direct irradiation from a source, it is envisioned that intraoperative irradiation of a target may be performed with the aid of nanoparticles. The use of nanoparticles, particularly nanoparticles with high atomic numbers (high-Z), enhances the administration of intraoperative irradiation. Nanoparticles with high-Z that are irradiated produce secondary short-range x-ray irradiation through the Auger-effect. The resultant scattered, short-range x-ray irradiation will increase DNA damage to cells containing or in close proximity to the nanoparticles while limiting the affect to other tissue and cells farther away. In a preferred embodiment, the high-Z nanoparticle is gold, though other high-Z nanoparticle materials that appropriately generate short-range irradiation are suitable. Other metal nanoparticles include titanium, bismuth, titanium dioxide, tin, tin oxide, iron, iron(III)oxide, silver, nickel, copper, and aluminum.

Suitable nanoparticles may be small enough to permeate a cell membrane but too large to permeate the cell's nuclear membrane (about 30 nm diameter), or small enough to permeate both the cell membrane and the cell's nuclear membrane (about 5 nm diameter). Smaller nanoparticles may provide a more potent Auger-effect than larger nanoparticles because secondary short-range emissions are more easily able to escape smaller nanoparticles.

The nanoparticles may be administered to the patient through an intravenous injection or by direct injection into the tumor or tumor bed. Accumulation of these nanoparticles within cancer cells and tumor tissues may be achieved passively by taking advantage of the enhanced permeability and retention of the vasculature in cancerous cells and tissue compared with non-cancerous tissue.

Transfection of the high-Z nanoparticles into tumor cells may be achieved by any of the known methods. In an embodiment, the nanoparticles are bound to carrier DNA, and the DNA-nanoparticle complex is enveloped in a liposome. The liposome can comprise any lipids or polymers that are able to be taken up by a eukaryotic cell membrane. Examples of suitable lipids include didodecyl dimethylammonium bromide, polyethyleneimine, poly(2-dimethylamino-ethylmethacrylate), poly(amido amine), and polyethylene glycol. In another embodiment, the nanoparticles may be transfected into cancer cells using electroporation, microinjection, or bolistics.

Further embodiments and uses of nanoparticles in conjunction with radiation therapy are described by PCT/EP2013/068002, which is incorporated in its entirety herein by reference.

Radiation and Immune Checkpoint Inhibition

The methods take advantage of irradiation therapy triggering the systemic or local antineoplastic immune effect. By applying a high dose to a target, the tumor cells do not migrate into apoptosis, but are physically destructed so that the tumor proteins and antigens are released. These released proteins and antigens can be absorbed by antigen presenting cells (APCs). The APCs present these absorbed tumor antigens to cytotoxic T-cells which detect tumor cells that carry similar proteins or antigens. The cytotoxic T-cells react with tumor cells presenting similar proteins or antigens, lysing the tumor cells. This immune response allows for an abscopal effect, in which the body's immune system targets both the cancerous tissue or cells at and distal to the site of irradiation.

Certain tumor-associated antigens are known to enable an immune response to tumor tissues and cancer cells. Such antigens specific for brain tumors include fragments derived from the interleukin-13 receptor α2, IL13α2, Mage-1, Aim-2, Isocitrate dehydrogenase 1, tyrosinase, tyrosinase-related protein 1, Trp-1, Trp-75, Trp-2, Gage, human melanoma-associated antigen p97/GP100, and melano-tranferrin. Antigens specific for breast cancers include Her2/neu. Antigens that are presented by multiple carcinomas include B-cyclin, EphA2/Eck, telomerase reverse transcriptase, NY-ESO, BAGE, GAGE, CDK4, hTert, Sart-1, survivin, GnT-V, and Mart-1. By lysing tumor cells with high irradiation these antigens and others may be released, thereby activating the patients anti-tumor immune response.

This radiation induced immune response to tumor cells may be enhanced by the co-treatment with pharmaceuticals or other therapies. In an embodiment, this co-treatment may be given before or immediately before administration of irradiation. In another embodiment, the co-treatment may be administered during the irradiation procedure. In another embodiment, the co-treatment may be administered after or immediately after the irradiation procedure. In an embodiment of the method, the irradiation is administered and the subsequent co-treatment is only administered after detecting an immune effect.

Suitable pharmaceuticals or other therapies include immune checkpoint inhibitors or other checkpoint blockade immunotherapies (CBI). Such compounds inhibit negative regulators of the immune response allowing a more robust immune response to result from the irradiation treatment. Appropriate pharmaceuticals to be used in CBI are known to persons of skill in the art. These CBI pharmaceuticals include at least those mentioned in Sharabi, A. B. et al. (2015) 29(5):331-340, which is incorporated in its entirety herein by reference. Such CBIs include sipuleucel-T, ipilimumab, pembrolizumab, nivolumab, tremelimuab, MPDL3280A, MEDI4736, lirilumab, BMS-986016, anti-PD1 compounds, anti-CTLA-4 compounds, pidilizumab, and atezolizumab. It is further envisioned that multiple CBIs may be administered to a patient who has or is going to undergo irradiation treatment. Co-treatment with multiple CBIs may be administered in combination or in succession, and any combination of CBIs or CBI doses may be used.

Post-Irradiation Immune Monitoring

An aspect of the instant method is monitoring a patient who has received irradiation therapy for confirmation of an immune effect. Traditional intraoperative irradiation is done after a tumor is resected or biopsied, and followed soon thereafter by the administration of subsequent chemotherapy and/or external radiation therapy. The subsequent administration of chemotherapy and/or external radiation therapy may depress the immune response induced by a high dose of irradiation. In order to optimize the treatment of a patient with high-dose irradiation, a patient may be monitored for an anti-tumor immune response after the irradiation. In an embodiment, post-treatment chemotherapy and/or external radiation therapy may be delayed until the monitoring of a patient who has previously received the irradiation therapy results in the detection of an anti-tumor immune response in the patient. In another embodiment, chemotherapy and/or external radiation therapy may be delayed indefinitely as a patient who has received irradiation therapy is monitored for an anti-tumor immune response.

Methods to monitor the development of anti-tumor immune responses in patients is known to one skilled in the art. Immune monitoring includes determining a patient's immune response by assaying the T-cells, B-cell, NK-cells or any other cells pertinent to the patient's immune response. Immune responses in patients may be either specific or multigenic, and may require detection methods intended to detect either or both of these responses.

Different classes of immune response monitoring include first-generation in vitro assays, second-generation ex vivo assays, and third-generation multifaceted assays. Descriptions of these assays are presented in Keilholz, U. et al. (2006) Clin. Cancer Res. 12(7 Suppl):2346s-2352s, which is incorporated in its entirety herein by reference. Any methods known in the art to monitor the immune response of patients having received high-dose irradiation therapy are suitable for the instant technology.

First-generation in vitro assays include proliferation assays in response to antigen exposure and the chromium release assay for toxicity. Both measure the T-cell response of a cell culture in vitro. In one assay the overall T-cell proliferation is measured after a bulk culture is exposed to an antigen target as determined by a [$^3$H]thymidine uptake. In another assay $^{53}$Cr release is measured after a bulk T-cell population is exposed to an effector population.

Second-generation ex vivo assays detect single-cell events. Flow cytometry assays detect T-cells whose receptors have been stained with a major histocompatibility complex (MHC) peptide multimers. Another second-generation assay may otherwise measure affinity of a T-cell with a specific epitope. A third second-generation assay measures the cytokine production capacity of T-cells in response to an antigen. An example of the cytokine whose production is measured is IFN-γ. Readouts for these second-generation assays include cytokine accumulation in T-cells whose secretion has been blocked or secretion of cytokines captured by antibodies bound to a cell surface, cyclosporine A assay, or plate. Another, preferred second-generation readout uses the enzyme-linked immune spot (ELISPOT) assay which allows for the detection of antigen-specific T-cells from a patient.

Third-generation assays detect T-cells by tetramers or cytokines flow cytometry (CFC) and determines other phenotypic and functional markers. One third-generation method is cytokine profiling using CFC which provides information on the presentation of type 1/type 2cytokines, such as IFNγ, IL-2, TNFα/IL-5, IL-13, or other tumor-associated cytokines. Another assay determines the memory or effector phenotype by using tetramer binding or CFC to determine surface expression of CD27, CD28, CD45RA, CCR7, and other tumor-associated molecules. Another third-generation assay determines cytotoxic capacity using a perforin or induction of CD107 surface expression readout detected by tetramers or CFC. Proliferative capacity can be determined using tetramers to provide a 5-(and-6)-carboxyfluorescein diacetate succinimidyl ester. Migratory phenotypes can be detected by tetramers or CFC to determine chemokine receptor and adhesion antigen presentation. Another third-generation assay uses tetramer dilutions or CFC with antigen dilutions to determine the response to serially diluted antigen concentrations. Any suitable tumor-associated antigen may be used including those disclosed in Zhang, J. G. et al. (2007) Clin. Cancer Res. 13(201):566-575, which is incorporated by reference herein in its entirety. Another assay uses tetramers to detect regulatory T-cells by detecting CD25, FOX-P3, IL-10 and other relevant markers.

Fourth-generation assays include whole-exome, whole-genome, and transcriptome sequencing to monitor immune response. In embodiments sequencing the transcriptome of tumor samples allows for the identification of both tumor-associated neoantigens or neoantigen epitopes and the tumor immune microenvironment. Comparison of tumor-derived sequence to non-tumor sequence identifies germline and somatic mutations. High neoantigen loads are significantly associated with immune responses. Any suitable tumor-associated neoantigens or neoantigen epitopes may be identified including those disclosed in Van Allen, E. M. et al. (2015) Science 350(6257):207-211, which is incorporated by reference herein in its entirety, or any other tumor-associated antigens. This sequencing method can also be used to identify the mutational loads of tumors, which are also strongly correlated with neoantigen loads. Levels of RNA expression of genes including granzyme A (GZMA) and perforin (PRF1) are associated with neoantigen loads and immune response, and can be characterized by the sequenced transcriptome of a tumor.

Any and all other appropriate assays known to persons of skill in the art may also be used to monitor an immune response. In one embodiment, immune response may be monitored using HMGB-1 levels in a patient's or recipient's serum (Gebhardt, C. et al. (2015) Clin. Cancer Res. 21(24): 5453-5459). Quantification of HMGB-1 levels can be performed by any appropriate method known in the art. In a one embodiment, HMGB-1 levels are determined by ELISA assays.

The immune response of a patient having received high dose irradiation therapy can be monitored by any of these monitoring methods, or by another method that is known in the art. Additionally, the immune response may be monitored by any combination of any two or more monitoring methods including methods that are classified in the same generation of assays or classified in different generations of assays.

EXAMPLE

Example 1

Background

Glioblastoma (GB) is treated with surgical resection followed by adjuvant radiochemotherapy and then maintenance chemotherapy. The time to recurrence following current standard-of care treatment is roughly seven months. Nearly all cancers progress, or recur, locally along the surgical margin, suggesting that augmenting local treatments may improve outcomes.

Methods

Intraoperative Radiotherapy in Glioblastoma Multiforme (INTRAGO) was a single-center, open-label, phase I/II dose-escalation trial that recruited adult patients with newly diagnosed GB amenable to resection. During surgery, all patients were treated with intraoperative radiotherapy (IORT) with low-energy photons (50 kV) at one of three dose levels. Dosing started at 20 Gy prescribed to the surgical margin and was escalated in 10 Gy increments up to 40 Gy. Patients then received standard adjuvant therapy consisting of concomitant external-beam radiotherapy (EBRT; 60 Gy in 30 fractions) and temozolomide (50 mg/m2/d) followed by maintenance temozolomide chemotherapy (150-200 mg/m2/d/cycle, 5/28 day schedule). The primary endpoint was safety as per occurrence of dose-limiting toxicities (DLT) within the first three months following IORT (wound healing defects, cerebral hemorrhage/ischemia, brain necrosis, and early termination of radiochemotherapy). Secondary endpoints were progression-free survival (PFS) and overall survival (OS). We also performed an exploratory analysis of the local PFS, defined as tumor recurrence within 1 cm of the treated surgical margin. The trial is registered at ClinicalTrials.gov, number NCT02104882.

Results

Between August 2013 and August 2015 15 patients with histologically confirmed isocitrate dehydrogenase wild-type GB were treated at three dose levels (n=7 at 20 Gy, n=4 at 30 Gy, n=4 at 40 Gy). Of these: 13 underwent incomplete resection; six had unresected multifocal tumors; and three did not receive per-protocol treatment (PPT). The MGMT promoter was not hypermethylated in ten patients. The median follow-up was 13.8 months. The majority of grade 3-5 adverse events (25 of 30) were deemed related to external-beam radiotherapy, chemotherapy, or tumor progression. Five patients developed suspected or confirmed radionecrosis. No IORT-related deaths occurred. The median PFS was 11.2 months (95% CI: 5.4-17.0) for all patients and 11.3 months (95% CI: 10.9-11.6) for those receiving PPT. The median local PFS was 14.3 m (95% CI: 8.4-20.2) for all patients and 17.8 m (95% CI: 9.7-25.9) for those receiving PPT. The median OS was 16.2 m (95% CI: 11.1-21.4) for all patients and 17.8 m (95% CI: 13.9-21.7) for those receiving PPT.

FIG. 1 displays the response in one patient to IORT. The initial MRI scan of this patient showed a T1-enhancing non-resectable satellite lesion located 1.1 cm dorsal to the tumor (red arrowheads). Residual tumor was detected in the resection cavity native (N) and contrast-enhanced (C) early post-operative MRI scans, indicated by white arrows. IORT was applied with 20 Gy (prescribed to the applicator surface, i.e. the cavity margin), resulting in sub-therapeutic doses of 1.5-2 Gy to the satellite lesion due to the steep dose gradient of low energy x-rays. Thirteen months from initial diagnosis, the satellite lesion was progressive, but cycling chemotherapy was not discontinued. However, subsequent scans showed weakening contrast enhancement consistent with distant response.

Conclusions

IORT with low-energy x-rays was associated with a highly relevant increase of progression-free survival and a manageable safety profile in a cohort with predominantly incompletely resected GB and unfavorable prognostic factors.

What is claimed is:

1. A method of treating cancer, comprising:
    administering a first dose of radiation to a subject having cancer;
    determining a level of a biomarker obtained from the subject after the administering, wherein the level indicates an immune response of the subject to the first dose;
    not administering a second dose of radiation to the subject when the level is at and/or not beyond a threshold value; and
    administering the second dose to the subject when the level is beyond the threshold value;
    wherein the level indicates an amount or an activity of at least one of interleukin-13 receptor α2, IL13α2, Mage-1, Aim-2, tyrosinase, tyrosinase-related protein 1, Trp-1, Trp-75, Trp-2, Gage, human melanoma-associated antigen p97/GP100, melano-tranferrin, Her2/neu, B-cyclin, EphA2/Eck, hTert, Sart-I, survivin, GnT-V, BAGE, CDK4, high mobility group box 1 protein, isocitrate dehydrogenase 1, NY-ESO, Mart-I, HMGB-1, PRFI, GZMA, or a specific fragment of any thereof.

2. The method of claim 1, wherein the first and second doses are part of a predetermined fractionated dose for the subject.

3. The method of claim 1, wherein the first and second doses are part of a predetermined hypofractionated dose for the subject.

4. The method of claim 1, wherein the first dose is part of a predetermined intraoperative dose to the subject.

5. The method of claim 1, wherein the second dose is not administered.

6. The method of claim 1, wherein the second dose is administered to a different location in the subject than was the first dose.

7. The method of claim 1, wherein the biomarker is obtained from at least one of serum, cerebrospinal fluid, peritoneal fluid, or urine.

8. The method of claim 1, wherein the cancer comprises a glioma.

9. The method of claim 1, wherein the administering the first dose is to a metastatic brain tumor.

10. The method of claim 1, wherein the first dose results in a target dose profile equivalent to administration of 3 Gy or greater administered at a target surface.

11. The method of claim 1, wherein the first dose results in a target dose profile equivalent to administration of between 3 Gy and 20 Gy administered at a target surface.

12. The method of claim 1, wherein the first dose results in a target dose profile equivalent to administration of between 5 Gy and 10 Gy administered at a target surface.

13. The method of claim 1, wherein the first dose results in a target dose profile equivalent to administration of between 20 Gy and 30 Gy administered at a target surface.

14. The method of claim 1, wherein the first dose results in a target dose profile equivalent to administration of between 30 Gy and 40 Gy administered at a target surface.

15. The method of claim 1, wherein the first dose results in a target dose profile equivalent to administration of between 20 Gy and 40 Gy administered at a target surface.

16. The method of claim 1, wherein the first dose results in a target dose profile equivalent to administration of one of 20 Gy, 30 Gy, or 40 Gy administered at a target surface.

* * * * *